US011564993B2

(12) United States Patent
Yuki et al.

(10) Patent No.: US 11,564,993 B2
(45) Date of Patent: Jan. 31, 2023

(54) INTRANASAL VACCINE THAT INDUCES CELLULAR IMMUNITY

(71) Applicants: The University of Tokyo, Tokyo (JP); HANAVAX INC., Tokyo (JP)

(72) Inventors: Yoshikazu Yuki, Tokyo (JP); Rika Nakahashi, Tokyo (JP); Hiroshi Kiyono, Tokyo (JP)

(73) Assignees: THE UNIVERSITY OF TOKYO, Tokyo (JP); HANAVAX INC., Tokyo (JP)

( * ) Notice: Subject to any disclaimer, the term of this patent is extended or adjusted under 35 U.S.C. 154(b) by 3 days.

Patent file contains an affidavit/declaration under 37 CFR 1.130(b).

(21) Appl. No.: 17/265,267

(22) PCT Filed: Aug. 2, 2019

(86) PCT No.: PCT/JP2019/030399
§ 371 (c)(1),
(2) Date: Feb. 2, 2021

(87) PCT Pub. No.: WO2020/027309
PCT Pub. Date: Feb. 6, 2020

(65) Prior Publication Data
US 2021/0308278 A1    Oct. 7, 2021

(30) Foreign Application Priority Data

Aug. 3, 2018  (JP) .............................. JP2018-146519

(51) Int. Cl.
| | |
|---|---|
| *A61K 47/69* | (2017.01) |
| *A61K 47/54* | (2017.01) |
| *A61P 37/04* | (2006.01) |
| *A61P 31/20* | (2006.01) |
| *A61P 31/14* | (2006.01) |
| *A61P 31/06* | (2006.01) |
| *A61K 39/04* | (2006.01) |
| *A61K 39/12* | (2006.01) |
| *A61K 39/155* | (2006.01) |
| *A61K 39/39* | (2006.01) |
| *C12N 7/00* | (2006.01) |
| *A61K 39/00* | (2006.01) |

(52) U.S. Cl.
CPC .......... *A61K 47/6903* (2017.08); *A61K 39/04* (2013.01); *A61K 39/12* (2013.01); *A61K 39/155* (2013.01); *A61K 39/39* (2013.01); *A61K 47/549* (2017.08); *A61P 31/06* (2018.01); *A61P 31/14* (2018.01); *A61P 31/20* (2018.01); *A61P 37/04* (2018.01); *C12N 7/00* (2013.01); *A61K 2039/55561* (2013.01); *C12N 2710/20034* (2013.01); *C12N 2760/18534* (2013.01)

(58) Field of Classification Search
None
See application file for complete search history.

(56) References Cited

U.S. PATENT DOCUMENTS

| | | |
|---|---|---|
| 6,566,516 B1 | 5/2003 | Sunamoto et al. |
| 6,656,481 B1 | 12/2003 | Shiku et al. |
| 2010/0310585 A1 | 12/2010 | Agger et al. |
| 2011/0206729 A1 | 8/2011 | Akiyoshi et al. |
| 2014/0205653 A1 | 7/2014 | Dubensky, Jr. et al. |
| 2016/0067334 A1 | 3/2016 | Weiner et al. |

FOREIGN PATENT DOCUMENTS

| | | | |
|---|---|---|---|
| JP | 5344558 | 8/2013 | |
| WO | 00/12564 | 3/2000 | |
| WO | 2017/170494 | 10/2017 | |
| WO | WO-2017170494 A1 * | 10/2017 | ............. A61K 39/00 |

OTHER PUBLICATIONS

Xin et al., PLoS ONE 8(8): e72745). (Year: 2013).*
Langley et al., JID vol. 218 pp. 378-387 (Year: 2018).*
Su et al. Biodrugs; 24 (2): 109-129). (Year: 2010).*
Nochi et al., Nature Materials 2010 vol 9, pp. 582-578 (Year: 2010).*
Azegami et al., Molecular Immunology vol. 98, pp. 19-24 (Year: 2018).*
Nishimura et al., "Trends and issues in mucosal vaccines, Igaku No Ayumi", 2018, vol. 264(5), pp. 411-418, with partial English translation.
Azegami et al., "Nanogel-based nasal vaccines for infectious and lifestyle-related diseases", Molecular Immunology, 2018, vol. 98, pp. 19-24.
Azegami et al., "Nanogel-based nasal ghrelin vaccine prevents obesity", Mucosal Immunology, 2017, vol. 10 (5), pp. 1351-1360.
Azegami et al., "Intranasal Vaccination against angiotensin II type 1 receptor and pneumococcal surface protein A attenuates hypertension and pneumococcal infection in rodents", Journal of Hypertension, 2018, vol. 36, pp. 387-394.
Aoshi et al., "Modes of action for mucosal vaccine adjuvants", Viral Immunology, 2017, vol. 30 (6), pp. 463-470.
Ayame et al., "Self-Assembled Cationic Nanogels for Intracellular Protein Delivery", Bioconjugate Chem., 2008, vol. 19, pp. 882-890.
Nochi et al., "Nanogel antigenic protein-delivery system for adjuvant-free intranasal vaccines", Nature Materials, 2010, vol. 9, 572-578.
Yuki et al., "Nanogel-based antigen-delivery system for nasal vaccines", Biotechnology and Genetic Engineering Reviews, 2013, vol. 29, pp. 61-72.

(Continued)

*Primary Examiner* — Shanon A. Foley
*Assistant Examiner* — Myron G Hill
(74) *Attorney, Agent, or Firm* — Wenderoth, Lind & Ponack, L.L.P.

(57) ABSTRACT

The present invention provides a nanogel nasal vaccine that induces cell-mediated immunity. The present invention relates to a vaccine preparation comprising a complex of a nanogel, a vaccine antigen, and an adjuvant, wherein the vaccine preparation can efficiently induce the cell-mediated immunity, and can also induce a systemic and mucosal immune response.

11 Claims, 5 Drawing Sheets

Specification includes a Sequence Listing.

(56) References Cited

OTHER PUBLICATIONS

Kong et al., "Nanogel-Based PspA Intranasal Vaccine Prevents Invasive Disease and Nasal Colonization by *Streptococcus pneumoniae*", Infection and Immunity, 2013, vol. 81, pp. 1625-1634.
International Search Report, dated Sep. 10, 2019 in corresponding International Patent Application No. PCT/JP2019/030399.
Extended European Search Report dated Jun. 22, 2022 in European Patent Application No. 19844843.3.
Fukuyama, Y. et al., "Nanogel-based pneumococcal surface protein A nasal vaccine induces microRNA-associated Th17 cell responses with neutralizing antibodies against *Streptococcus pneumoniae* in macaques", Mucosal Immunology, vol. 8, No. 5, Sep. 2015, pp. 1144-1153.
Nagatomo, Daiki et al., "Cholesteryl Pullulan Encapsulated TNF-α Nanoparticles Are an Effective Mucosal Vaccine Adjuvant against Influenza Virus", BioMed Research International, vol. 2015, Jan. 1, 2015, pp. 1-15, XP055900035.

\* cited by examiner

[Figure 1]
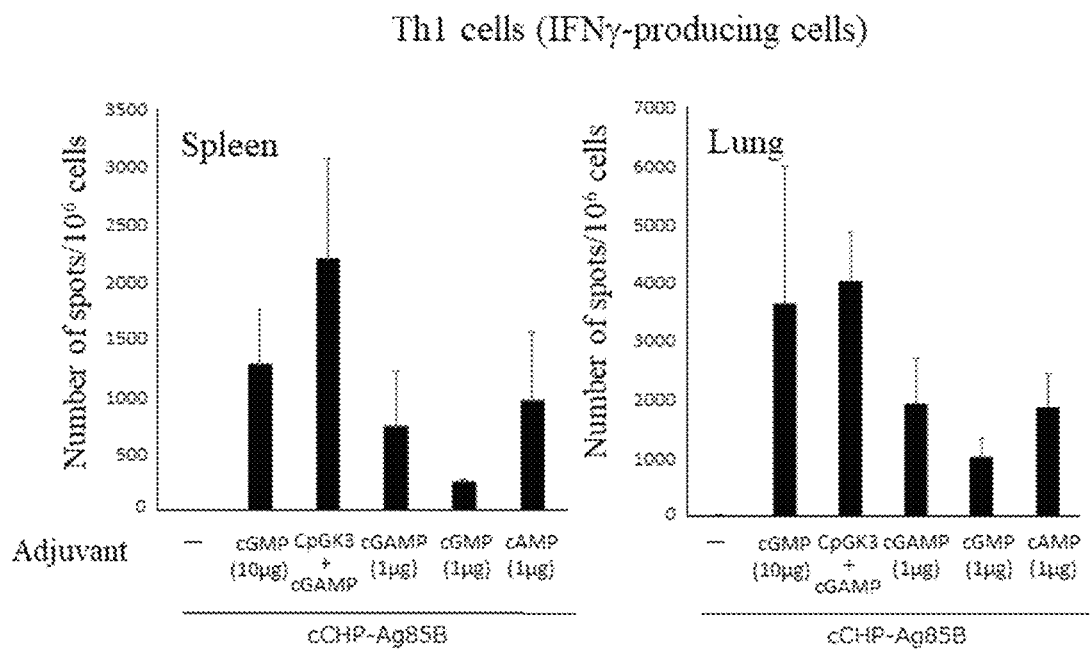
[Figure 2]
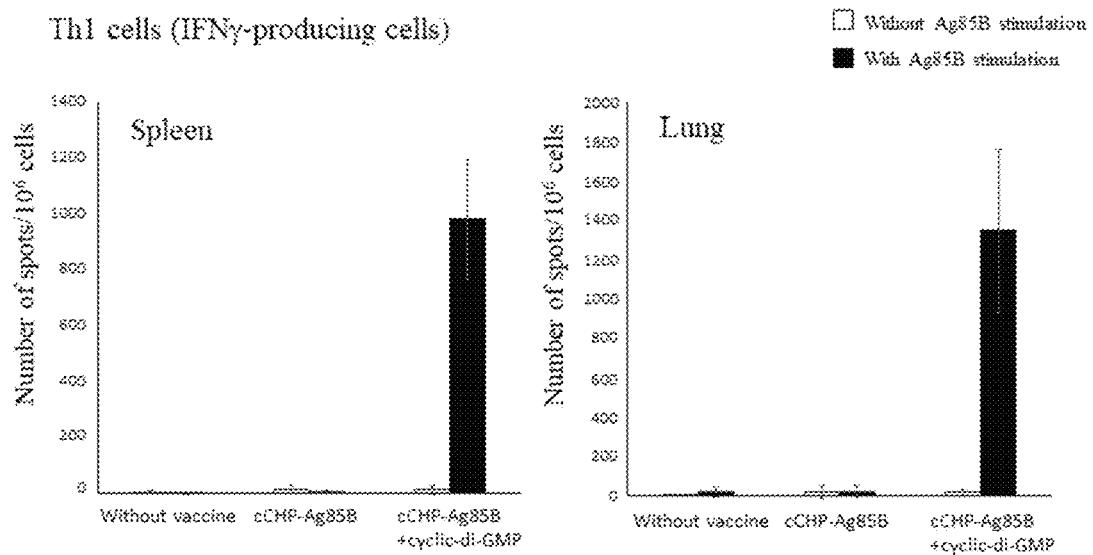

[Figure 3]
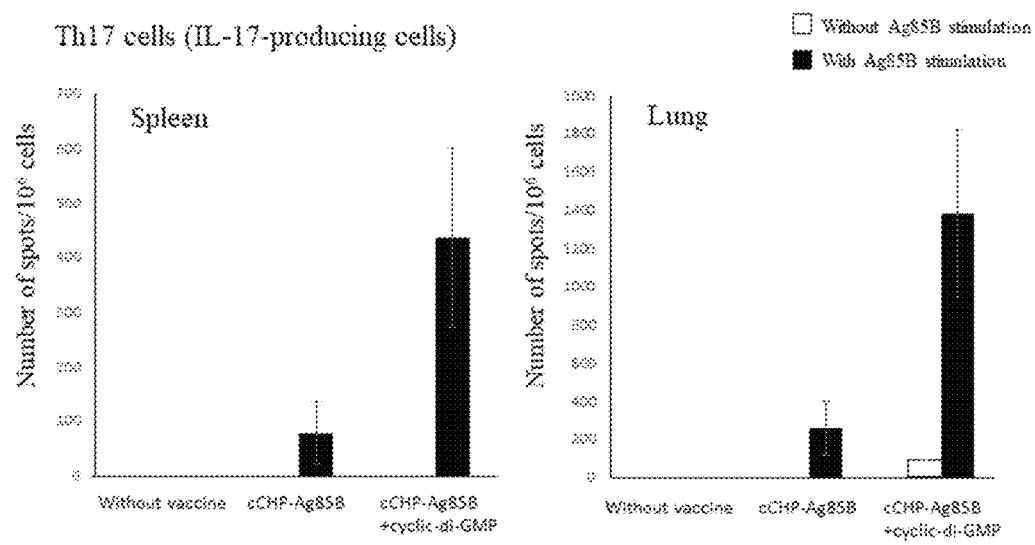
[Figure 4]
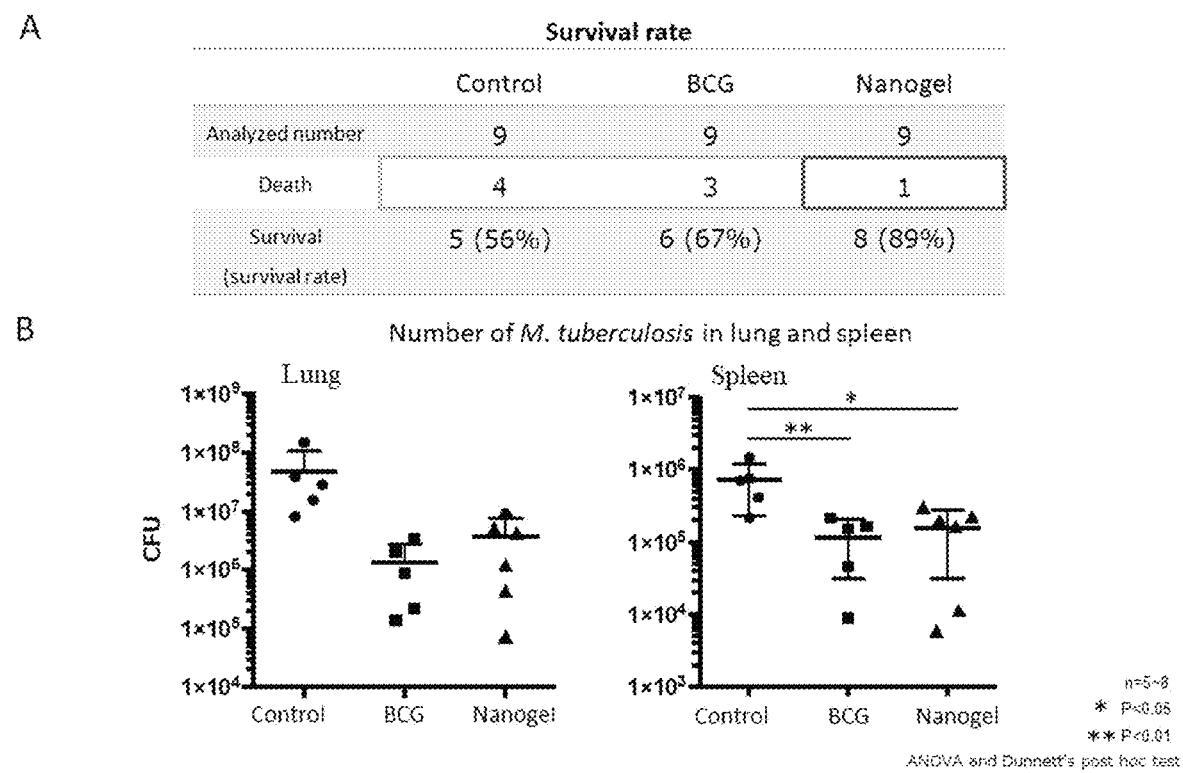

[Figure 5]
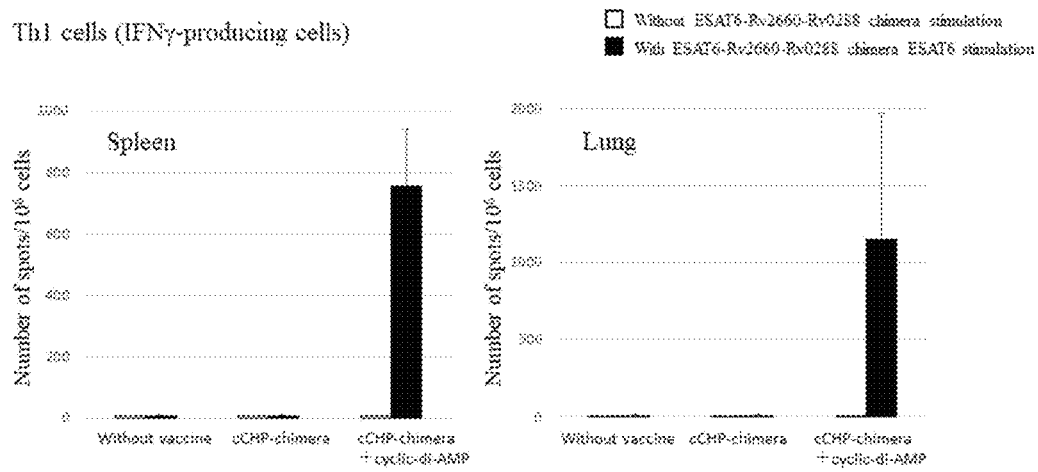
[Figure 6]
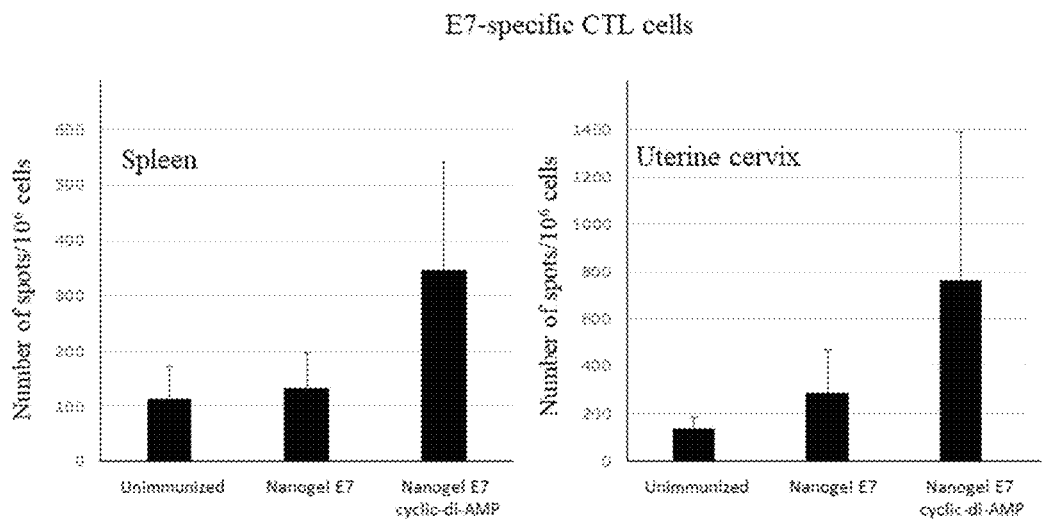

[Figure 7]
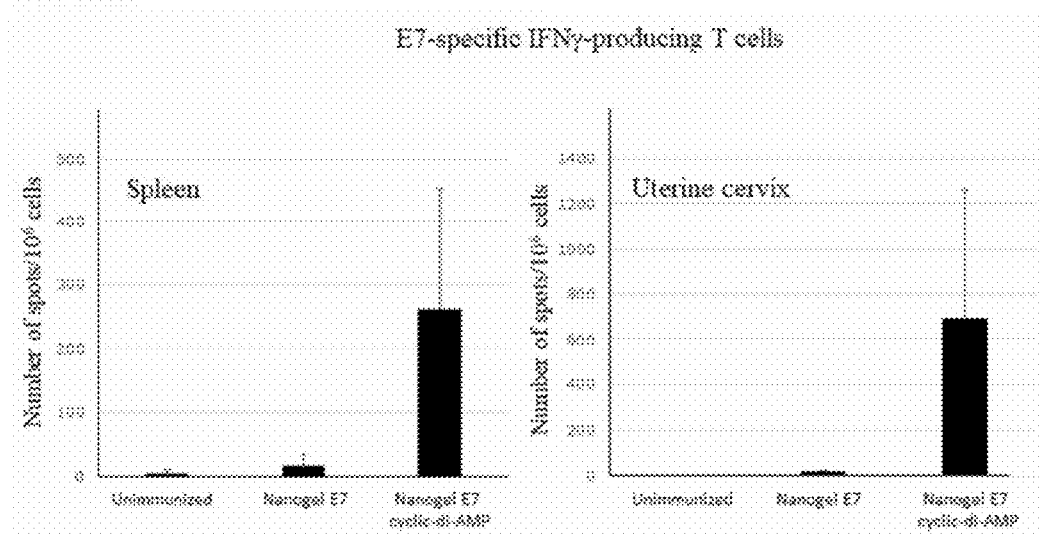
[Figure 8]
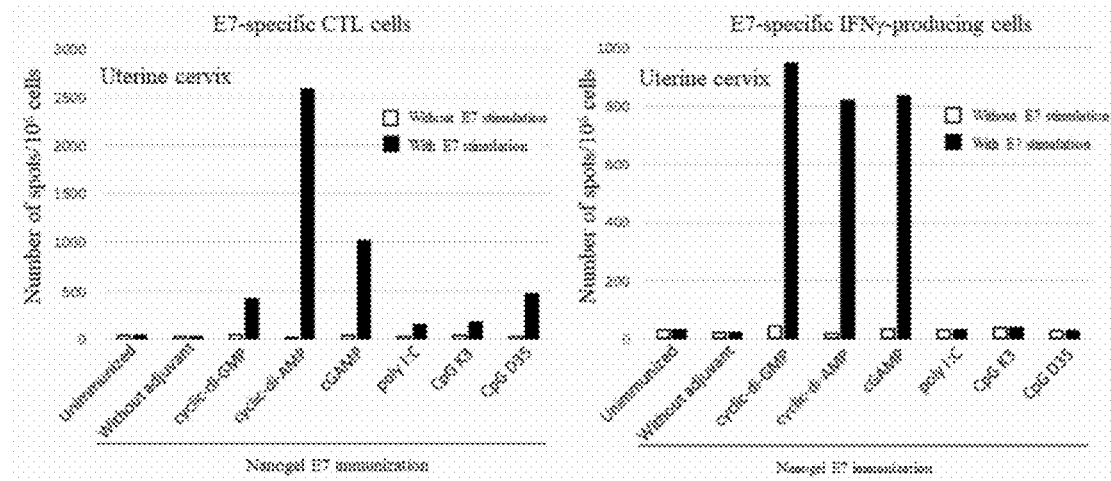

[Figure 9]
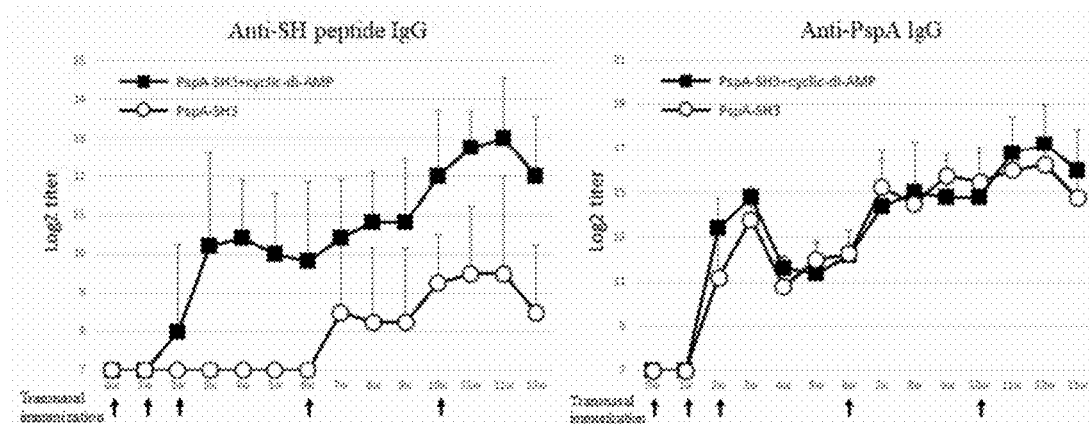
[Figure 10]
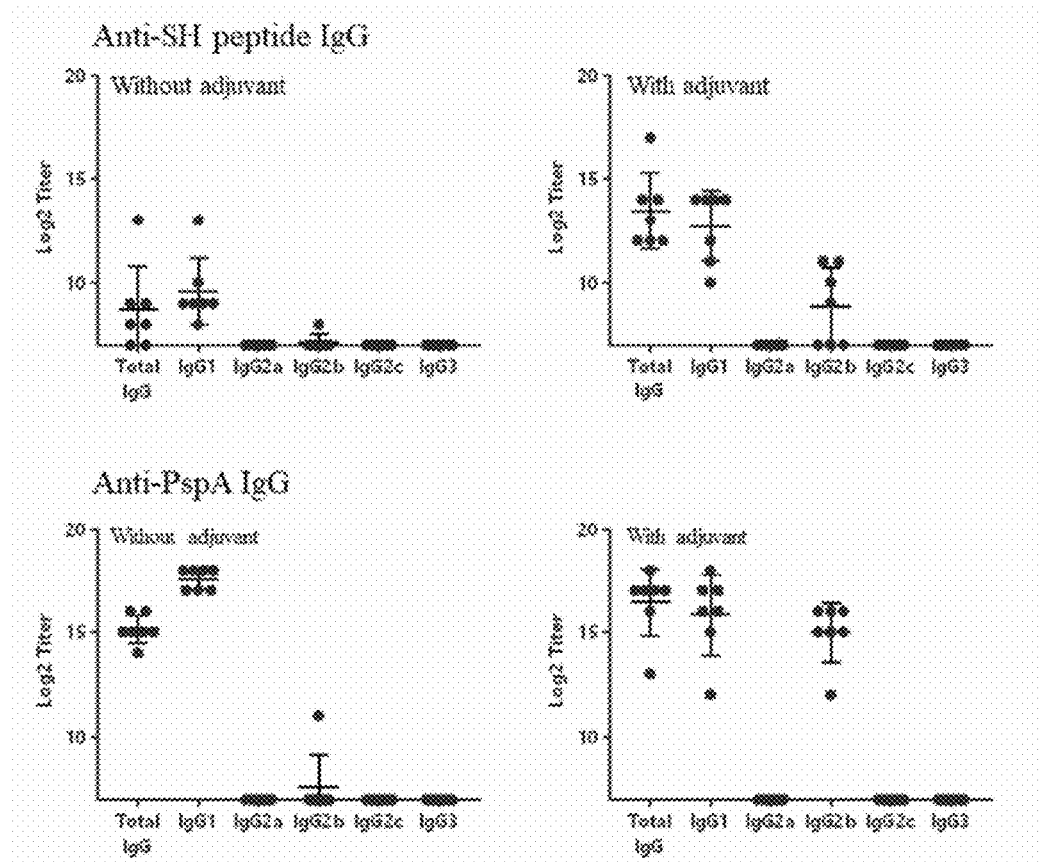

INTRANASAL VACCINE THAT INDUCES CELLULAR IMMUNITY

TECHNICAL FIELD

The present invention relates to a nasal vaccine that induces cell-mediated immunity.

BACKGROUND ART

Acquired immunity is played by two different mechanisms, namely, humoral immunity and cell-mediated immunity.

Humoral immunity is an immune system mainly involving antibodies, complements and the like that are present in blood. If a foreign antigen invades into a living body, the foreign antigen is taken in an antigen-presenting cell such as a dendritic cell and is then fragmented. Thereafter, the thus fragmented antigen is presented on the surface of the cell via an MHC class II molecule. Thereafter, a Th2 cell stimulated by the antigen-presenting cell recognizes the antigen fragment presented on a B cell via a T cell antigen receptor (TCR) and then performs the release of a Th2 cytokine, etc. The B cell produces an antibody, in response to the action of the released Th2 cytokine.

On the other hand, cell-mediated immunity is an immune system for eliminating foreign matters from a living body by macrophages, cytotoxic T lymphocytes (CTL), natural killer cells, etc. If a Th1 cell is activated by an antigen fragment presented on an antigen-presenting cell via an MHC class II molecule, the Th1 cell releases IFN-γ and activates a macrophage. Moreover, the Th1 cell induces not a neutralizing antibody but an antibody binding to the cell surface, and activates a macrophage or an NK cell via an Fc receptor of the antibody, so that the macrophage or the NK cell attacks and destroys a target cell. Thus, induction of antibody-dependent-cellular-cytotoxicity (ADCC) is also considered. In addition, the activated Th1 cell releases IL-2 and activates CTL that recognizes the presented antigen fragment together with an MHC class I molecule. The activated macrophage and CTL attack cells infected with viruses and the like, cancer cells, etc., and eliminate them. Since cell-mediated immunity is also able to eliminate infected cells, cancer cells, etc., it is expected that the cell-mediated immunity will be applied to elimination of *Mycobacterium tuberculosis* that can be parasitic in cells, or to cancer immunotherapy.

To date, the present inventors have developed an effective vaccine delivery system by utilizing self-aggregating nano-sized hydrogel constituted with cationic type of cholesteryl group-bearing pullulan (cCHP) (Patent Literature 1 and Non Patent Literature 1). When a cCHP nanogel includes a protein antigen in the nanomatrix thereof, it functions as an artificial chaperone, prevents aggregation and degeneration of the antigen, and helps refolding after the release of the antigen. This nanogel has the property of efficiently adhering to the surface of a negatively charged mucosa. The nanogel continuously releases antigens and delivers the antigens to antigen-presenting cells, so as to induce immune response (Non Patent Literature 2, Non Patent Literature 3, and Patent Literature 2). Furthermore, in the case of mice, although a cCHP nanogel that carries [$^{111}$In]-labeled BoHc/A (the heavy chain C-terminal nontoxic region of botulinum toxin type A) or pneumococcal surface antigen PspA is transnasally administered to the mice, it is not accumulated in the central nerve system such as olfactory bulb or brain (Non Patent Literature 2), and the safety thereof has been confirmed (Non Patent Literature 4).

A nanogel vaccine suitable for transnasal administration (i.e., a nanogel nasal vaccine) is extremely favorable in terms of both safety and induction of humoral immunity. However, it has not been confirmed so far that such a nanogel nasal vaccine induces cell-mediated immunity.

CITATION LIST

Patent Literature

Patent Literature 1: WO00/12564
Patent Literature 2: Japanese Patent No. 5344558

Non Patent Literature

Non Patent Literature 1: Ayame et al., Bioconjug Chem 19: 882-890, 2008
Non Patent Literature 2: Nochi et al., Nat Mater 9: 572-578, 2010
Non Patent Literature 3: Yuki et al., Biotechnol Genet Eng Rev 29: 61-72, 2013
Non Patent Literature 4: Kong et al., Infect Immun 81: 1625-1634 2013

SUMMARY OF INVENTION

Technical Problem

Considering the aforementioned circumstances, it is an object of the present invention to provide a nanogel nasal vaccine that induces cell-mediated immunity.

Solution to Problem

In order to achieve the above-described object, the present inventors have produced a vaccine, in which a STING ligand used as an adjuvant, as well as a vaccine antigen, is included in a nanogel, and then, have transnasally administered the produced vaccine to mice. As a result, the present inventors have succeeded in inducing antigen-specific Th1 cells.

Specifically, the present invention includes the following (1) to (11).

(1) A vaccine preparation comprising a complex of a nanogel, a vaccine antigen, and an adjuvant.
(2) The vaccine preparation according to the above (1), wherein the adjuvant comprises one or more STING ligands.
(3) The vaccine preparation according to the above (2), wherein at least one of the STING ligands is a cyclic dinucleotide.
(4) The vaccine preparation according to the above (3), wherein the cyclic dinucleotide is any one of cGAMP cyclic-di AMP, cyclic-di GMP, cyclic-di CMP, cyclic-di UMP, or cyclic-di IMP.
(5) The vaccine preparation according to any one of the above (1) to (4), wherein the vaccine antigen is an antigen derived from *Mycobacterium tuberculosis*.
(6) The vaccine preparation according to the above (5), wherein the *Mycobacterium tuberculosis*-derived antigen comprises, at least, all or a part of an Ag85B gene product, an Rv2608 gene product, an Rv3619 gene product, an Rv3620 gene product, an Rv1813 gene product, an MTB32A gene product, an MTB39A gene product, and/or an MVA85A gene product.
(7) The vaccine preparation according to the above (5), wherein the *Mycobacterium tuberculosis*-derived antigen is a chimeric protein consisting of an Rv3875 gene product, an Rv0266 gene product, and an Rv0288 gene product.

(8) The vaccine preparation according to any one of the above (1) to (4), wherein the vaccine antigen is an HPV (human papillomavirus)-derived antigen.
(9) The vaccine preparation according to the above (8), wherein the HPV-derived antigen comprises, at least, all or a part of an E6 gene product and/or an E7 gene product.
(10) The vaccine preparation according to any one of the above (1) to (4), wherein the vaccine antigen is an RSV (respiratory syncytial virus)-derived antigen.
(11) The vaccine preparation according to the above (10), wherein the RSV-derived antigen comprises, at least, all or a part of an SH peptide.

Advantageous Effects of Invention

By administration of the nanogel vaccine according to the present invention, cell-mediated immunity can be induced.
By administration of the nanogel vaccine according to the present invention, both systemic immune response and mucosal immune response can be efficiently induced.

BRIEF DESCRIPTION OF DRAWINGS

FIG. 1 shows the results of detecting a Th1 cell response induced by a nanogel *Mycobacterium tuberculosis* nasal vaccine and a STING ligand. The terms "cGMP," "cGAMP" and "cAMP" indicate cyclic-di-GMP, cyclic-GMP-AMP, and cyclic-di-AMP, respectively. -: without vaccine; cCHP: cationic cholesteryl-group bearing pullulan.

FIG. 2 shows the results of detecting a Th1 cell response induced by a nanogel *Mycobacterium tuberculosis* nasal vaccine.

FIG. 3 shows the results of detecting a Th7 cell response induced by a nanogel *Mycobacterium tuberculosis* nasal vaccine.

FIG. 4 shows studies regarding protective immune effects induced by a nanogel *Mycobacterium tuberculosis* nasal vaccine. FIG. 4A shows a survival rate, and FIG. 4B shows the number of *Mycobacterium tuberculosis* detected in lung and spleen. "Control" indicates an unimmunized mouse group, "BCG" indicates a BCG vaccination group, and "Nanogel" indicates a cCHP-Ag85B+cyclic-di-GMP vaccination group.

FIG. 5 shows the results of detecting a Th1 cell response induced by a nanogel *Mycobacterium tuberculosis* nasal vaccine (chimeric antigen).

FIG. 6 shows the results of detecting a CTL cell response induced by a nanogel HPV nasal vaccine.

FIG. 7 shows the results of detecting a Th1 cell response induced by a nanogel HPV nasal vaccine.

FIG. 8 shows a comparison between a CTL cell response (left) and a Th1 cell response (right) induced by a nanogel HPV nasal vaccine using three types of STING ligands as adjuvants.

FIG. 9 shows the results of detecting an immune response induced by a nanogel RSV nasal vaccine.

FIG. 10 shows the results of detecting IgG subclasses induced by a nanogel RSV nasal vaccine.

DESCRIPTION OF EMBODIMENTS

A first embodiment of the present invention relates to a vaccine preparation comprising a complex of a nanogel, a vaccine antigen, and an adjuvant (hereinafter also referred to as "the vaccine preparation of the present invention").

In the present invention, the term "nanogel" is used to mean polymeric gel nanoparticles, in which a hydrophobic cholesterol is added as a side chain to a hydrophilic polysaccharide (e.g., pullulan). Such nanogel can be produced according to a known method, such as the method described, for example, in International Publication WO00/12564.

Specifically, first, a hydroxyl group-containing hydrocarbon having 12 to 50 carbon atoms or a sterol is allowed to react with a diisocyanate compound represented by OCN—R1 NCO (wherein R1 represents a hydrocarbon group having 1 to 50 carbon atoms) to produce an isocyanate group-containing hydrophobic compound, with which a single molecule of the hydroxyl group-containing hydrocarbon having 12 to 50 carbon atoms or sterol is reacted. The obtained isocyanate group-containing hydrophobic compound is allowed to react with a polysaccharide to produce a hydrophobic group-containing polysaccharide comprising a hydrocarbon group having 12 to 50 carbon atoms or a steryl group. Subsequently, the obtained product is purified in a ketone-based solvent to produce a hydrophobic group-containing polysaccharide with a high purity.

As a polysaccharide used herein, pullulan, amylopectin, amylose, dextran, hydroxyethyl dextran, mannan, levan, inulin, chitin, chitosan, xyloglucan, water-soluble cellulose, etc. can be utilized, and pullulan is particularly preferable.

Examples of the nanogel used in the first embodiment of the present invention may include cationic cholesteryl-group-bearing pullulan (referred to as "cCHP") and a derivative thereof. The cCHP has a structure, in which 1 to 10 cholesterols, preferably, one to several cholesterols are substituted per 100 monosaccharides in pullulan having a molecular weight of 30.000 to 200,000, for example, having a molecular weight of 100,000. Besides, the cCHP used in the present invention may be changed, as appropriate, in terms of the amount of cholesterols substituted, depending on the size of an antigen or the degree of hydrophobicity. In addition, in order to change the degree of hydrophobicity of the CHP, an alkyl group (having approximately 10 to 30, preferably approximately 12 to 20 carbon atoms) may be added to the CHP. The nanogel used in the present invention has a particle diameter of 10 to 40 nm, and preferably of 20 to 30 nm. The nanogels have already been widely marketed, and such commercially available nanogel products may also be used.

The nanogel used in the embodiment of the present invention is a nanogel into which a functional group having a positive charge, such as, for example, an amino group, is introduced, so that a vaccine can invade in the surface of the negatively charged nasal mucosa. As a method of introducing an amino group into a nanogel, a method of using an amino group-added cholesterol pullulan ($CHPNH_2$) can be applied. Specifically, CHP dried under reduced pressure is dissolved in dimethyl sulfoxide (DMSO), and 1,1'-carbonyldiimidazole is then added to the obtained solution under a nitrogen air current, followed by performing a reaction at room temperature for several hours. Thereafter, ethylenediamine is gradually added to the reaction solution, and the obtained mixture is then stirred for several hours to several tens of hours. The obtained reaction solution is dialyzed against distilled water for several days. After completion of the dialysis, the reaction solution is freeze-dried to obtain an opalescent solid. The substitution degree of ethylenediamine can be evaluated using elemental analysis, H-NMR, etc.

The vaccine antigen is not particularly limited, and can be arbitrarily selected depending on the intended use of a vaccine preparation. In particular, since the vaccine preparation of the present invention can efficiently induce cell-mediated immunity, the present vaccine preparation is significantly suitably used for activation of a cell-mediated immune system for prevention or treatment of diseases, etc. If such diseases are purposely exemplified, examples of the diseases may include: tuberculosis, for which no effective vaccines for adults are present; nontypeable *Haemophilus influenzae* (NTHi), RSV (respiratory syncytial virus) infection, or HSV (herpes simplex virus) infection, for which no vaccines are present; and HPV (human papilloma virus) infection, for the treatment of which induction of cell-mediated immunity is considered to be important, and cervical cancer developed by infection with the HPV The vaccine antigen against tuberculosis is not particularly limited. For example, the vaccine antigen against tuberculosis may be a *Mycobacterium tuberculosis*-derived Ag85B (Rv1886) gene product, ESAT6 (Rv3875) gene product, Rv2660 gene product, Rv2608 gene product, Rv3619 gene product, Rv3620 gene product, Rv1813 gene product, MTB32A (Rv0125) gene product, MTB39A (Rv1196) gene product, MVA85A gene product, or Rv0288 gene product, as a whole or a part thereof, or a plurality of fusion proteins selected from these proteins (e.g., a chimeric protein of an ESAT6-Rv2660-Rv0288 gene product).

The vaccine antigen against nontypeable *Haemophilus influenzae* (NTHi) may be D15, P1, P2, P4, P5, P6, Hmv/hia, Hap, Protein E, Protein F, Protein D, Pil A. NucA, HtrA, OMP26, PCP, TbpB, or LOS, as a whole or a part thereof, or a plurality of fusion proteins selected from these proteins.

The vaccine antigen against RSV is not particularly limited. For example, the vaccine antigen against RSV may be an RSV-derived F protein (fusion protein) or SH protein as a whole or a part thereof, or a plurality of fusion proteins selected from these proteins.

The vaccine antigen against HSV is not particularly limited. For example, the vaccine antigen against HSV may be an HSV-derived gD gene product, gB gene product, gC gene product, gE gene product, capsid protein UL19, Tegment protein UL47, or gG gene product, as a whole or a part thereof, or a plurality of fusion proteins selected from these proteins.

The vaccine antigen against HPV is not particularly limited. For example, the vaccine antigen against HPV may be an HPV-derived E6 gene product, and in particular, a E6 gene product comprising a mutation or deletion of the site that tumor suppressor gene products P53 bind to, an HPV-derived E7 gene product, and in particular, a E7 gene product comprising a mutation or deletion of the site that tumor suppressor gene products P53 bind to. More specifically, the vaccine antigen against HPV may be HPV6 E7 (23-27 deleted), HPV11 E7 (23-27 deleted), HPV16 E7 (D21G, C24G, and E26G mutated), HPV16 E7 (21-24 deleted), HPV18 E7 (24-27 deleted), HPV31 E7 (22-26 deleted), HPV33 E7 (22-26 deleted), HPV45 E7 (26-30 deleted), HPV52 E7 (22-26 deleted), HPV52 E7 (22-26 deleted), or HPV58 E7 (22-26-deleted), as a whole or a part thereof, or a plurality of fusion proteins selected from these proteins.

The adjuvant used in the embodiment of the present invention has the same definitions as those of agents referred to as an "antigenic reinforcement," an "inmnunostimulator," and the like. The present adjuvant is used for the general intended use of these agents in the present technical field. The active ingredient of the adjuvant used in the embodiment of the present invention is not particularly limited. Examples of the active ingredient of the present adjuvant may include STING ligands that activate STING (stimulator of interferon genes) (e.g., cyclic dinucleotides such as cGAMP, cyclic-di AMP, cyclic-di GMP, cyclic-di CMP, cyclic-di UMP, or cyclic-di IMP, and xanthenone derivatives such as DMXAA (5,6-dimethylXAA (xanthenone-4-acetic acid), Vadimezan, or ASA404), poly IC, and CpG ODN. The present adjuvant may further comprise pharmaceutically acceptable carriers or other components (e.g., stabilizers, pH adjusters, preservatives, antiseptics, buffers, etc.). It is necessary that such pharmaceutically acceptable carriers and other components are substances that do not affect the health of an animal administered with a vaccine.

A complex of a nanogel, a vaccine antigen, and an adjuvant (or an active ingredient of the adjuvant, same as below) can be produced by allowing a nanogel, a vaccine antigen, and an adjuvant to coexist, allowing them to interact with one another, and incorporating the antigen and the adjuvant into the nanogel. At this time, the mixing ratio of the nanogel and the vaccine antigen and the mixing ratio of the nanogel and the adjuvant are not particularly limited, and these mixing ratios can be easily determined by a person skilled in the art according to preliminary experiments. If the guidelines of such mixing ratios are purposely exemplified, the mixing ratio of the vaccine antigen:the nanogel is, for example, approximately 0.1:10, 1:5, 1:2, or 1:1, at a molar ratio. In addition, regarding the content of the adjuvant, the adjuvant may be comprised in an amount of approximately 0.01% by weight to 99.99% by weight, with respect to 100% by weight of the vaccine. The content of the adjuvant may be, for example, approximately 0.01 weight to 10 weights, with respect to 1 weight of the antigen.

The complex of a nanogel, a vaccine antigen, and an adjuvant can be formed by mixing the nanogel, the vaccine antigen, and the adjuvant, and then leaving the obtained mixture at rest at a temperature of 4° C. to 50° C., for example, at 40° C., for 30 minutes to 48 hours, for example, for approximately 1 hour. The buffer used to form the complex of a nanogel, a vaccine antigen, and an adjuvant is not particularly limited, and if the buffer is purposely exemplified, it may be, for example, a Tris-HCl buffer.

When the vaccine preparation of the present invention is used as a composition (the vaccine composition of the present invention), it may comprise pharmaceutically acceptable additives. The vaccine preparation of the present invention is suitable for transnasal administration, and the dosage form thereof is desirably a form that can be administered via transnasal administration. Examples of the dosage form of the present vaccine preparation may include liquid preparations (nasal drops, injections, etc.).

When the vaccine preparation of the present invention is a liquid preparation, the active ingredient may be dissolved in distilled water for preparations, as necessary, together with a pH adjuster such as hydrochloric acid, sodium hydroxide, lactose, lactic acid, sodium, sodium monohydrogen phosphate or sodium dihydrogen phosphate, and a tonicity agent such as sodium chloride or glucose, and the obtained solution may be subjected to aseptic filtration and then, the resulting solution may be filled into an ampoule. Otherwise, mannitol, dextrin, cyclodextrin, gelatin or the like may be further added to the resulting solution, followed by vacuum-freeze drying, so as to produce a preparation of extemporaneous dissolution type. The present liquid preparation may comprise pharmaceutically acceptable, known stabilizers, antiseptics, antioxidants, etc. Examples of the stabilizers may include gelatin, dextran, and sorbitol. Examples of the antiseptics may include thimerosal and β propiolactone. An example of the antioxidants may be α tocopherol.

A second embodiment of the present invention relates to a method for preventing and/or treating a disease, wherein the method comprises transnasal administration of a vaccine preparation comprising a complex of a nanogel, a vaccine antigen, and an adjuvant (first embodiment) to a patient.

The target disease of the treatment or prevention of the second embodiment is not particularly limited, and it depends on the type of the vaccine antigen used. The target disease may include cancers (e.g., cervical cancer), as well as infections caused by pathogens (e.g., tuberculosis. HSV, RSV, etc.). The target disease includes all diseases, which are expected to be recovered by cell-mediated immunity.

The vaccine preparation of the present invention may be administered to a patient through the nasal mucosa. The administration method may be, for example, a method of administering the vaccine preparation into the nasal cavity by spraying, coating, dropping or the like of the vaccine preparation onto the nasal mucosa.

The applied dose of the mucosal vaccine preparation can be determined, as appropriate, depending on the age, body weight and the like of an administration target. The mucosal vaccine preparation comprises a pharmaceutically effective amount of vaccine antigen. The pharmaceutically effective amount means the amount of an antigen that is necessary for induction of an immune response to the vaccine antigen. The vaccine preparation may be administered to a target, for example, at a single applied dose of vaccine antigen of several µg to several tens of mg, once to several times per day, with intervals of one to several weeks, several times in total, for example, 1 to 5 times.

The disclosures of all publications cited in the present description are incorporated herein by reference in their entireties. In addition, throughout the present description as a whole, when singular terms with the article "a," "an." and "the" are used, these terms include not only single items but also multiple items, unless otherwise clearly specified from the context.

Hereinafter, the present invention will be further described in the following examples. However, these examples are only illustrative examples of the embodiments of the present invention, and thus, are not intended to limit the scope of the present invention.

EXAMPLES

Methods
1. *Mycobacterium tuberculosis* Vaccine
1-1. Preparation of Antigen Protein A *Mycobacterium tuberculosis* (ATCC25618)-derived Ag85B gene (987 bp) (SEQ ID NO: 1) was artificially synthesized, and was then inserted into the EcoRI-HinIII (Takara Bio, Inc.) site of a pET-20b(+) vector (Novagen) having a His-Tag sequence gene. The produced expression vector was transformed into Rosetta2 (DE3) pLysS-*Escherichia coli* according to an ordinary method. The obtained transformant was cultured in a medium containing 100 µg/mL ampicillin and 34 µg/mL chloramphenicol at 37° C., until the value of OD 600 nm became 0.5 to 0.8. Thereafter, 1.0 mM isopropyl β-D-1-thiogalactopyranoside (Wako Pure Chemical Industries, Ltd.) was added to the culture, and the obtained mixture was then cultured for 4 hours. Thereafter, the cultured *Escherichia coli* was recovered by centrifugation (5,000 rpm, 15 minutes). The recovered *Escherichia coli* was washed with a solution containing 10 mM imidazole and a protease inhibitor (Roche Diagnostics), and the protein was then extracted with an adsorption buffer containing 20 mM Tris-HCl, 500 mM NaCl, 10 mM imidazole, and 6 M urea. The extracted protein fraction was charged into a nickel affinity column (GE Healthcare Bio-Sciences), and was then washed with the adsorption buffer until the value of OD 280 nm became 0.01 or less. After that, the protein was eluted using a solution containing 20 mM Tris-HCl, 500 mM NaCl, 500 mM imidazole, and 6 M urea. Subsequently, the eluant was concentrated with Amicon, and was then subjected to gel filtration using a Sephacryl S-100 column (GE Healthcare Bio-Sciences) equilibrated with 6 M-Urea PBS. Thereafter, an Ag85B fraction was recovered, and was then dialyzed stepwise against 4 M-Urea PBS, 2 M-Urea PBS, and 1 M-Urea PBS, PBS, so as to prepare native Ag85B. 50 mg of Ag85B (SEQ ID NO: 2) was recovered from 12 L of the *Escherichia coli* culture, and the purity was measured to be 95% by SDS-PAGE.

1-2. Formation of Nanogel Comprising Antigen (Preparation of Vaccine)

A cCHP nanogel was prepared according to the method reported in the previous publication (Non Patent Literature 2).

The prepared cCHP nanogel and the purified Ag85B protein were mixed with each other at a molecular ratio of 1:1, and further, three types of STING ligands (cyclic-di-GMP, cyclic-di-AMR and cGAMP) were each added as adjuvants to the mixture, followed by performing incubation using a heat block at 40° C. for 1 hour.

On the other hand, the cCHP nanogel and the purified chimeric protein (ESAT6-Rv2660c-Rv0288) (amino acid sequences: SEQ ID NO: 8:and nucleic acid sequence: SEQ ID NO: 9) were mixed with each other at a molecular ratio of 1:1, and further, a STING ligand (cyclic-di-AMP) was added as a mucosal adjuvant to the mixture, followed by performing incubation using a heat block at 40° C. for 1 hour.

1-3. Transnasal Immunization to Mice

A cCHP-Ag85B+STING ligand mixed solution was transnasally administered to 7-week-old female Balb/c mice. With regard to the single dose of the antigen administered per mouse, 10 µg of the antigen was administered to each mouse, in terms of the amount of the Ag85B protein. On the other hand, the STING ligand was prepared in the amount range of 1 µg to 10 µg per mouse, and was then administered. Such transnasal immunization was cared out a total of three times with intervals of 1 week.

At the same time, a cCHP-chimera+STING ligand solution was transnasally administered to 7-week-old female Balb/c mice. With regard to the single dose of the antigen administered per mouse, 10 µg of the antigen was administered to each mouse, in terms of the amount of the chimeric protein. On the other hand, the STING ligand was administered at a single dose of 10 µg per mouse. Such transnasal immunization was carried out a total of three times with intervals of 1 week.

1-4. Purification and Counting of Antigen-Specific T Cells
(1) Ag85B Antigen

Two weeks after the final vaccination, antigen-specific Th1 cells (IFNγ-producing cells) or Th17 cells (IL-17-producing cells) were counted according to an ELISPOT method. The systemic immune response was evaluated using the spleen, whereas the immune response on the mucosal surface was evaluated using antigen-specific T cells generated in lung tissues.

The mice were euthanized. The lung and the spleen were excised from the mice, and cell suspensions were then prepared. From the prepared cell suspensions, CD4-positive T cells were purified using MACS system (Miltenyi Biotec). On the other hand, from unimmunized mouse spleen, CD90.2-negative cells were purified in the same manner as described above, and the purified cells were used as antigen-presenting cells. The CD4-positive T cells and the antigen-presenting cells irradiated with gamma rays were co-cultured under stimulation with the purified Ag85B antigen for 48 to 72 hours. In this culture operation, an anti-IFNγ antibody or an anti-IL-17 antibody had previously been adsorbed as a capture antibody on the bottom of the culture well.

Thereafter, the culture supernatants and the cells were removed, and the wells were then washed. A biotin-labeled anti-IFNγ antibody or anti-IL-17 antibody was added to the wells, and a reaction was then performed at room temperature for 2 hours. Thereafter, the wells were washed, were then reacted with streptavidin HRP, followed by washing. Thereafter, 3-amino-9-ethylcarbazole (AEC) that was a substrate of HRP was added to the wells for color development, and antigen-specific Th1 cells or Th17 cells were then detected as spots. The number of spots was counted using an ELISpot Counter.

(2) ESAT6-Rv2660c-Rv0288 Chimeric Antigen

Two weeks after the final administration, the number of antigen-specific Th1 cells (IFNγ-producing cells) was counted according to an ELISPOT method. The systemic immune response was evaluated using the spleen, whereas the immune response on the mucosal surface was evaluated using antigen-specific T cells generated in lung tissues.

The mice were euthanized. The lung and the spleen were excised from the mice, and cell suspensions were then prepared. From the prepared cell suspensions, CD4-positive T cells were purified using magnetic beads. On the other hand, from unimmunized mouse spleen, CD90.2-negative cells were purified in the same manner as described above, and the purified cells were used as antigen-presenting cells. The CD4-positive T cells and the antigen-presenting cells irradiated with gamma rays were co-cultured under stimulation with the purified chimeric antigen or recombinant ESAT6 (Abcam) for 48 to 72 hours. An anti-IFNγ was spread as a capture on the bottom of the culture wells, and the producing cells were detected.

The culture supernatants were removed, the wells were then washed, and a biotin-labeled anti-IFNγ antibody was then reacted with the residues. The wells were further washed, were then reacted with streptavidin HRP, followed by washing. Thereafter, 3-amino-9-ethylcarbazole (AEC) that was a substrate of HRP was added to the wells for color development, and antigen-specific Th1 cells were then detected as spots. The number of spots was counted using an ELISpot Counter.

1-5. Studies Regarding Protective Immune Effects (1) Vaccination to Mice

As mice, 7-week-old female Balb/c mice were used. A BCG vaccine used as a positive control was suspended in a PBS solution, and it was subcutaneously administered to the mice once at the time of initial immunization. With regard to the single dose of a mixed solution of cCHP-Ag85B+cyclic-di-GMP administered per mouse, 10 μg of the Ag85B protein was transnasally administered to each mouse a total of three times with intervals of 1 week. To unimmunized control mice, PBS was transnasally administered three times every other week, and at the time of initial immunization, PBS was subcutaneously administered once.

(2) Sinopulmonary Infection with *Mycobacterium tuberculosis* Virulent Strain

Eight weeks after the final vaccination, the mice were infected with the *Mycobacterium tuberculosis* virulent strain Erdman via sinopulmonary infection at a dose of 100 CFU per mouse.

(3) Counting the Number of *Mycobacterium tuberculosis* in Spleen and Lung Tissues Twelve weeks after the infection, the mice were euthanized, and the lung and the spleen were then excised. The tissues were disintegrated and suspended in PBS, and six dilution series were prepared. The prepared dilution series were each seeded on an agar medium. Culture was carried out for 4 weeks in an anaerobic environment, colonies were then counted, and the number of *Mycobacterium tuberculosis* in individual tissues was then calculated.

2. Preparation of HPV Vaccine 2-1. Preparation of Antigen Protein

An HPV16 E7 virus gene with 3 amino acid mutations D21G, C24G and E26G of tumor suppressor gene products (Van der Burg S H et. al. Vaccine 19: 3652-3660, 2001) (307 bp) (SEQ ID NO: 3) was artificially synthesized, and was then inserted into the EcoRI-HinIII (Takara Bio, Inc.) site of a pET-20b(+) vector (Novagen) having a His-Tag sequence gene. The produced expression vector was transformed into Rosetta2 (DE3) pLysS-*Escherichia coli* according to an ordinary method. The obtained transformant was cultured in a medium containing 100 μg/mL ampicillin and 34 μg/mL chloramphenicol at 37° C., until the value of OD 600 nm became 0.5 to 0.8. Thereafter, 1.0 mM isopropyl β-D-1-thiogalactopyranoside (Wako Pure Chemical Industries, Ltd.) was added to the culture, and the obtained mixture was then cultured for 4 hours. Thereafter, the cultured *Escherichia coli* was recovered by centrifugation (5,000 rpm, 15 minutes). The recovered *Escherichia coli* was washed with a solution containing 10 mM imidazole and a protease inhibitor (Roche Diagnostics), and the protein was then extracted with an adsorption buffer containing 20 mM Tris-HCL, 500 mM NaCl, 10 mM imidazole, and 6 M urea. The extracted protein fraction was charged into a nickel affinity column (GE Healthcare Bio-Sciences), and was then washed with the adsorption buffer until the value of OD 280 nm became 0.01 or less. After that, the protein was eluted using a solution containing 20 mM Tris-HCl, 500 mM NaCl, 500 mM imidazole, and 6 M urea. Subsequently, the eluant was dialyzed against 6M Urea-PBS (0.15M NaCl) and was then adsorbed on a DEAE-sepharose column (GE Healthcare Bio-Sciences K.K) equilibrated with the same buffer as described above, and thereafter, it was eluted with a solution containing 0.5 M NaCl-PBS-6 M Urea. The obtained eluant was concentrated with Amicon, and was then subjected to gel filtration using a Sephacryl S-100 column (GE Healthcare Bio-Sciences) equilibrated with 6 M-Urea PBS. Thereafter, a mutant E7 fraction was recovered, and was then dialyzed stepwise against 4 M-Urea PBS, 2 M-Urea PBS, 1 M-Urea PBS, and PBS, so as to prepare native mutant E7 (SEQ ID NO: 4). Thereafter, 60 mg of the mutant E7 was recovered from 12 L of the *Escherichia coli* culture, and the purity was measured to be 95% by SDS-PAGE.

2-2. Formation of Nanogel Comprising Antigen (Preparation of Vaccine)

A cCHP nanogel was prepared according to the method reported in the previous publication (Non Patent Literature 2).

The prepared cCHP nanogel and the purified mutant E7 protein were mixed with each other at a molecular ratio of 1:1, and further, cyclic-di-AMP alone, three types of STING ligands (cyclic-di-GMP, cyclic-di-AMP, and cGAMP), poly I:C, or CpG ODN K3 type or D35 type was each added as an adjuvant to the mixture, followed by performing incubation using a heat block at 40° C. for 1 hour.

2-3. Transnasal Immunization to Mice

A mixed solution of cCHP-mutant E7+each mucosal adjuvant was transnasally administered to 7-week-old female Balb/c mice. With regard to the single dose of the antigen administered per mouse, 10 μg of the antigen was administered to each mouse, in terms of the amount of the mutant E7 protein. On the other hand, each mucosal adjuvant was administered at a single dose of 5 μg or 10 μg to each mouse. Such transnasal immunization was carried out a total of three times with intervals of 1 week.

2-4. Purification and Counting of Antigen-Specific T Cells (1) In the Case of Using Cyclic-Di-AMP as Adjuvant One week after the final vaccination, antigen-specific CTL cells (granzyme B-producing cells) or Th1 cells (IFNγ-producing cells) were counted according to an ELISPOT method. The systemic immune response was evaluated using the spleen, whereas the immune response in genital mucosa was evaluated using antigen-specific T cells induced in the cervix.

The mice were euthanized. The spleen and the cervix were excised from the mice, and cell suspensions were then prepared. From the prepared cell suspensions, T cells (CD90.2-positive) were purified using MACS system (Miltenyi Biotec). On the other hand, from unimmunized mouse spleen, CD90.2-negative cells were purified in the same manner as described above, and the purified cells were used as antigen-presenting cells. The purified T cells and the antigen-presenting cells irradiated with gamma rays were co-cultured under stimulation with the purified mutant E7 antigen for 48 to 72 hours. In this culture operation, an anti-granzyme B antibody or an anti-IFNγ antibody had previously been adsorbed as a capture antibody on the bottom of the culture well.

Thereafter, the culture supernatants and the cells were removed, and the wells were then washed. A biotin-labeled anti-granzyme B antibody or anti-IFNγ antibody was added to the wells, and a reaction was then performed at room temperature for 2 hours. Thereafter, the wells were washed, were then reacted with streptavidin HRP, followed by washing. Thereafter, 3-amino-9-ethylcarbazole (AEC) that was a substrate of HRP was added to the wells for color development, and antigen-specific CTL cells or Th1 cells were then detected as spots. The number of spots was counted using an ELISpot Counter.

(2) In the Case of Using Three Types of STING Ligands (Cyclic-Di-GMP, Cyclic-Di-AMP, and cGAMP) as Adjuvants One week after the final vaccination, antigen-specific Th1 cells (IFNγ-producing cells) and CTL cells (granzyme B-producing cells) in the cervix were counted according to an ELISPOT method. The mice were euthanized. The cervix was excised from the mice, and cell suspensions were then prepared. Thereafter, using magnetic beads, T cells (CD90.2-positive) were purified from the cell suspensions. On the other hand, from unimmunized mouse spleen, CD90.2-negative cells were purified in the same manner as described above, and the purified cells were used as antigen-presenting cells. The purified T cells and the antigen-presenting cells irradiated with gamma rays were co-cultured under stimulation with the purified mutant E7 antigen for 48 to 72 hours. An anti-IFNγ antibody or an anti-granzyme B antibody or was added as a capture antibody on the bottom of the culture well, and the producing cells were detected.

Thereafter, the culture supernatants were removed, and the wells were then washed. A biotin-labeled anti-IFNγ antibody or anti-granzyme B antibody was added to and reacted with the residue. The wells were further washed, and were then reacted with streptavidin HRP, followed by washing. Thereafter, AEC that was a substrate of HRP was added to the wells for color development, and antigen-specific CTL cells or Th1 cells were then detected as spots. The number of spots was counted using an ELISpot Counter.

3. Preparation of RSV Vaccine 3-1. Preparation of Antigen Protein

A DNA sequence (1172 bp), in which three PspA were repeatedly added to the SH peptide (SEQ ID NO: 5) of an RSV virus via linkers (GGGGS) (SEQ ID NO: 7), was artificially synthesized, and then, using the restriction enzymes EcoRV and NotI (Takara Bio, Inc.), the DNA sequence was inserted into a pET-20b(+) vector (Novagen) having a gene of a His-Tag sequence. This plasmid was transformed into Rosetta2(DE3)pLysS-*Escherichia coli* according to an ordinary method. The resulting *Escherichia coli* was cultured in a medium containing 100 μg/mL ampicillin and 34 hg/mL chloramphenicol at 37° C. until the value of OD 600 nm became 0.5 to 0.8. Thereafter, 1.0 mM isopropyl β-D-1-thiogalactopyranoside (Wako Pure Chemical Industries, Ltd.) was added to the culture, and the obtained mixture was further cultured for 4 hours. Thereafter, the resulting *Escherichia coli* was recovered by centrifugation (5000 rpm, 15 minutes). The recovered *Escherichia coli* was washed with a solution containing 20 mM imidazole and a protease inhibitor (Roche Diagnostics), and the protein was then extracted with an adsorption buffer containing 20 mM Tris-HCl, 500 mM NaCl, and 10 mM imidazole. A saturated ammonium sulfate solution was added to the extract, so that it became 80% saturated, and ammonium sulfate precipitation was then carried out. The precipitate was recovered by centrifugation, and was then dialyzed, using, as an external fluid, the same buffer as that used upon the extraction. The fluid obtained after completion of the dialysis was charged into a nickel affinity column (GE Healthcare Bio-Sciences), and was then washed with the adsorption buffer, until the value of OD 280 nm became 0.01 or less, followed by elution with a solution containing 20 mM Tris-HCl, 500 mM NaCl, and 500 mM imidazole. The eluant was concentrated with Amicon, and was then subjected to gel filtration using a Sephadex G-100 column (GE Healthcare Bio-Sciences) equilibrated with PBS. Thereafter, a PspA-SH3 fraction was recovered, and was then concentrated and purified. After that, 70 mg of PspA-SH3 was recovered from 20 L of the *Escherichia coli* culture, and the purity was measured to be 95% by SDS-PAGE.

3-2. Formation of Nanogel Comprising Antigen (Preparation of Vaccine)

The cCHP nanogel and the purified PspA-SH3 protein (SEQ ID NO: 6) were mixed with each other at a molecular ratio of 1:1, and further, cyclic-di-AMP was added as a mucosal adjuvant to the mixture, followed by performing incubation using a heat block at 40° C. for 1 hour.

3-3. Transnasal Immunization to Mice

A mixed solution of cCHP-PspA-SH3+cyclic-di-AMP was transnasally administered to 7-week-old female Balb/c mice. With regard to the single dose of the antigen administered per mouse, 10 μg of the antigen was administered to each mouse, in terms of the amount of the PspA-SH3 protein. In addition, cyclic-di-AMP was administered at a dose of 10 μg to each mouse. Such transnasal immunization was carried out in a total of five times, namely, three times with intervals of 1 week, then, once after an interval of 4 weeks, and then, once after an interval of 4 weeks.

3-4. Measurement of Antibody Titer

Every week, approximately 100 μl of blood was collected from the submandibular vein, and was then centrifuged at 15000 rpm at 4° C. to recover serum.

The measurement of IgG antibody titer in PspA- or SH-specific serum and the measurement of IgG subclasses were carried out by an ELISA method. One day before implementation of the ELISA, PspA or BSA conjugate SH was diluted with PBS to a concentration of 1 μg/ml, and 100 μl each of the obtained solution was then dispended as a capture into a 96-well plate (Thermo scientific, 3355), followed by performing incubation at 4° C. overnight. Using a plate washer, the plate was washed with 300 μl of 0.05% Tween (Nacalai Tesque, 28353-85)-containing PBS (PBS-T) four times, and 1% BSA (Nacalai Tesque, 01863-48)-containing PBS-T was then added to the plate in an amount of 200 μL/well. Incubation was carried out at room temperature for 1 hour, and the wells were blocked. Subsequently, using a plate washer, the plate was washed with 300 μl of PBS-T three times. Each sample diluted with 1% BSA-containing PBS-T to $2^8$ fold was added to the wells at one end of the plate, and two-fold serial dilution was then carried out until the other end of the plate, so as to produce serial dilution series. Then, incubation was carried out at room temperature for 2 hours. 1% BSA-containing PBS-T was set to be a blank. After completion of the incubation, using a plate washer, the plate was washed with 300 μL of PBS-T four times. Subsequently, any of 6 types of Goat anti-Human IgG, IgG1, IgG2a, IgG2b, IgG2c, and IgG3 (Southern Biotech), which had been 4000-fold diluted with 1% BSA-containing PBS-T, was added to the plate in an amount of 100 μl/well, and incubation was then carried out at room temperature for 1.5 hours. Thereafter, using a plate washer, the plate was washed with 300 μl of PBS-T four times. A TMB substrate mixed with a TMB solution (Seracare, 5120-0050) in equal amounts was added to the plate in an amount of 100 μl/well, and a coloring reaction was then carried out for 30 minutes. Thereafter, 50 μl of 2 N $H_2SO_4$ (Nacalai Tesque, 32520-55) was added to the reaction mixture to terminate the reaction. The OD 450 value was measured using a plate reader, and the log 2 titer value was then calculated. The cutoff value was set to be the mean value of the blank well +0.1.

Results

1. *Mycobacterium tuberculosis* Vaccine (1) Ag85B Antigen

When compared with the case of addition of a mixture consisting of 10 μg of CpGK3 known to exhibit adjuvant activity and 1 μg of cGAMP as one type of STING ligand, the same level of induction of antigen-specific Th1cell-mediated immunity was observed by addition of 10 μg of cyclic-di-GMP (FIG. 1). When a comparison was made in terms of the single use of a STING ligand (cAMP, GMP, or cGAMP), cyclic-di-AMP (cAMP) was considered to be relatively effective.

Subsequently, the effect of inducing Th1 cells and Th17 cells by using a STING ligand as an adjuvant was examined. Cyclic-di-GMP was used as a STING ligand. In the case of mice, to which a vaccine antigen not containing Cyclic-di-GMP had been administered, almost neither antigen-specific Th1 cell nor Th17 cells were induced (FIG. 2 and FIG. 3, "cCHP-Ag85B"). In addition, even in a case where antigen-presenting cells were not stimulated with an antigen, almost no T cells were induced. On the other hand, it was found that, in the lung and the spleen, the antigen-specific Th1 cells and Th17 cells were significantly induced by transnasal administration of cCHP-Ag85B-cyclic-di-GM, and that both systemic immune response and mucosal immune response were efficiently induced (FIG. 2 and FIG. 3).

The nanogel nasal vaccine of the present invention, comprising a STING ligand as an adjuvant, was administered to mice. In this case, the influence of the present nanogel nasal vaccine on the survival rate and proliferation of *Mycobacterium tuberculosis* was examined, while using a BCG vaccine as a positive control. During a period from infection until 12 weeks, several fatal cases were observed. From such fatal cases, the survival rate was calculated. As a result, compared with the survival rate of unimmunized mice (negative control) that was 56% and the survival rate of the BCG vaccine group (positive control) that was 67%, the nanogel group (administration of cCHP-Ag85B+cyclic-di-GMP) had a survival rate of 89% and thus, exhibited resistance to the infection (FIG. 4A). Moreover, with regard to the number of *Mycobacterium tuberculosis* in the spleen, proliferation of *Mycobacterium tuberculosis* was significantly suppressed equally in the BCG group and in the nanogel vaccine group, compared with the unimmunized mice. The same tendency was observed even in the lung (FIG. 4B).

(2) ESAT6-Rv2660c-Rv0288 Chimeric Antigen

It was found that antigen-specific Th1 cells were induced in the spleen and the cervix by transnasal administration of cCHP-chimera+cyclic-di-AMP (FIG. 5). On the other hand, such antigen-specific Th1 cells were not induced in any organ by administration of cCHP-chimera alone. Accordingly, it was considered that cyclic-di-AMP would be essential for the Th1 cells.

2. HPV Vaccine (1) In the Case of Using Cyclic-Di-AMP as Adjuvant

Using an HPV mutant E7 protein as an antigen, the nanogel nasal vaccine of the present invention was produced, and the effect of this vaccine to induce T cells and the like was examined.

It was found that antigen-specific CTL cells were induced in the spleen and the cervix by transnasal administration of cCHP-mutant E7+cyclic-di-AMP (FIG. 6). In addition, it was also found that antigen-specific Th1 cells were induced in the spleen and the cervix by transnasal administration of the cCHP-mutant E7+cyclic-di-AMP (FIG. 7).

(2) In the Case of Using Three Types of STING Ligands (Cyclic-Di-GMP, Cyclic-Di-AMP, and cGAMP) as Adjuvants It was found that antigen-specific Th1 (FIG. 8, right) and CTL (FIG. 8, left) were induced in the cervix, by using a mucosal adjuvant combined with a cCHP-mutant E7protein antigen, and in particular, by transnasal immunization combined with three types of STING ligands. In the induction of Th1, no large difference was found among the STING ligands. In the induction of CTL, strong induction of CTL by cyclic-di-AMP was observed.

3. RSV Vaccine

It was found that the amounts of both an antibody against an SH peptide and an antibody against PspA as a carrier protein increase over time, depending on the number of transnasal immunizations (FIG. 9). Moreover, regarding an SH peptide-specific immune response, IgG was more significantly induced in a group to which cyclic-di-AMP had been added (FIG. 9, left). However, even in a group to which only cCHP-PspA-SH3 had been administered without cyclic-di-AMP, induction of the specific antibody was observed in a manner dependent on the number of immunizations.

Regarding IgG subclasses, in both cases of the anti-SH peptide and anti-PspA antibodies, IgG1 was preferentially induced without a cyclic-di-AMP adjuvant, and IgG1 and IgG2b were preferentially induced with the adjuvant (FIG. 10).

As described above, when an adjuvant (which is a STING ligand in the present example) was included in a nanogel vaccine and the vaccine was then administered, T cells characterized by cell-mediated immunity, such as Th1 cells or CLT cells, were induced. Moreover, it became clear that not only systemic immunity, but also mucosal immunity in genital mucosal tissues, as well as in upper and lower respiratory tract mucosal tissues, was induced by administration of the vaccine.

INDUSTRIAL APPLICABILITY

Since the nanogel nasal vaccine of the present invention is able to induce cell-mediated immunity, it is expected that the present nanogel nasal vaccine will be utilized in medical field such as cellular immunotherapy.

60

The invention claimed is:

1. A vaccine preparation comprising a complex of a nanogel, a vaccine antigen, and an adjuvant.

2. The vaccine preparation according to claim 1, wherein the adjuvant comprises one or more STING ligands.

3. The vaccine preparation according to claim 2, wherein at least one of the STING ligands is a cyclic dinucleotide.

4. The vaccine preparation according to claim 3, wherein the cyclic dinucleotide is any one of cGAMP, cyclic-di AMP, cyclic-di GMP, cyclic-di CMP, cyclic-di UMP, or cyclic-di IMP.

5. The vaccine preparation according to claim 2,
wherein the vaccine antigen is an antigen derived from *Mycobacterium tuberculosis*, and
wherein the antigen derived from *Mycobacterium tuberculosis* comprises an Ag85B gene product, an Rv2608 gene product, an Rv3619 gene product, an Rv3620 gene product, an Rv1813 gene product, an MTB32A gene product, an MTB39A gene product, an MVA85A gene product, and/or a chimeric protein consisting of an Rv3875 gene product, an Rv2660 gene product, and an Rv0288 gene product.

6. The vaccine preparation according to claim 2,
wherein the vaccine antigen is an HPV (human papillomavirus)-derived antigen, and
wherein the HPV-derived antigen comprises an HPV6 E7 gene product, an HPV6 E7 (23-27 deleted) gene product, an HPV11 E7 (23-27 deleted) gene product, an HPV16 E7 (D21G, C24G, and E26G mutated) gene product, an HPV16 E7 (21-24 deleted) gene product, an HPV18 E7 (24-27 deleted) gene product, an HPV31 E7 (22-26 deleted) gene product, an HPV33 E7 (22-26 deleted) gene product, an HPV45 E7 (26-30 deleted) gene product, an HPV52 E7 (22-26 deleted) gene product, an HPV52 E7 (22-26 deleted) gene product, and/or an HPV58 E7(22-26-deleted) gene product.

7. The vaccine preparation according to claim 2,
wherein the vaccine antigen is an RSV (respiratory syncytial virus)-derived antigen, and
wherein the RSV-derived antigen comprises an SH peptide.

8. A method for preventing and/or treating infections, comprising:
transnasal administration of a vaccine preparation according to claim 5 to a patient.

9. A method for preventing and/or treating infections, comprising:
transnasal administration of a vaccine preparation according to claim 6 to a patient.

10. A method for preventing and/or treating infections, comprising:
transnasal administration of a vaccine preparation according to claim 7 to a patient.

11. A method for preventing and/or treating cervical cancer, comprising:
transnasal administration of a vaccine preparation according to claim 6 to a patient.

* * * * *

SEQUENCE LISTING

<160> NUMBER OF SEQ ID NOS: 9

<210> SEQ ID NO 1
<211> LENGTH: 975
<212> TYPE: DNA
<213> ORGANISM: Mycobacterium tuberculosis

<400> SEQUENCE: 1

```
atgacagacg tgagccgaaa gattcgagct tggggacgcc gattgatgat cggcacggca      60
gcggctgtag tccttccggg cctggtgggg cttgccggcg gagcggcaac cgcgggcgcg     120
ttctcccggc cggggctgcc ggtcgagtac ctgcaggtgc cgtcgccgtc gatgggccgc     180
gacatcaagg ttcagttcca gagcggtggg aacaactcac ctgcggttta tctgctcgac     240
ggcctgcgcg cccaagacga ctacaacggc tgggatatca cacccgcc gttcgagtgg      300
tactaccagt cgggactgtc gatagtcatg ccggtcggcg ggcagtccag cttctacagc     360
gactggtaca gcccggcctg cggtaaggct ggctgccaga cttacaagtg ggaaaccttc     420
ctgaccagcg agctgccgca atggttgtcc gccaacaggg ccgtgaagcc caccggcagc     480
gctgcaatcg gcttgtcgat ggccggctcg tcggcaatga tcttggccgc ctaccacccc     540
cagcagttca tctacgccgg ctcgctgtcg gccctgctgg acccctctca ggggatgggg     600
cctagcctga tcggcctcgc gatgggtgac gccggcggtt acaaggccgc agacatgtgg     660
ggtccctcga gtgacccggc atgggagcgc aacgaccccta cgcagcagat ccccaagctg     720
gtcgcaaaca cacccggct atgggtttat tgcgggaacg gcaccccgaa cgagttgggc     780
ggtgccaaca tacccgccga gttcttggag aacttcgttc gtagcagcaa cctgaagttc     840
caggatgcgt acaacgccgc gggcgggcac aacgccgtgt tcaacttccc gcccaacggc     900
acgcacagct gggagtactg gggcgctcag ctcaacgcca tgaagggtga cctgcagagt     960
tcgttaggcg ccggc                                                      975
```

<210> SEQ ID NO 2
<211> LENGTH: 325
<212> TYPE: PRT
<213> ORGANISM: Mycobacterium tuberculosis

<400> SEQUENCE: 2

```
Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80
```

Gly Leu Arg Ala Gln Asp Asp Tyr Asn Gly Trp Asp Ile Asn Thr Pro
            85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
            115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ala Met Ile Leu Ala
            165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
            195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
            245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
            275                 280                 285

Gly His Asn Ala Val Phe Asn Phe Pro Pro Asn Gly Thr His Ser Trp
            290                 295                 300

Glu Tyr Trp Gly Ala Gln Leu Asn Ala Met Lys Gly Asp Leu Gln Ser
305                 310                 315                 320

Ser Leu Gly Ala Gly
            325

<210> SEQ ID NO 3
<211> LENGTH: 294
<212> TYPE: DNA
<213> ORGANISM: Human papillomavirus type 16

<400> SEQUENCE: 3
atgcatggag atacacctac attgcatgaa tatatgttag atttgcaacc agagacaact      60
ggcctctacg gctatggcca attaagtgac agctcagagg aggaggatga aatagatggt     120
ccagctggac aagcagaacc ggacagagcc cattacaata ttgtaacctt ttgttgcaag     180
tgtgactcta cgcttcggtt gtgcgtacaa agcacacacg tagacattcg tactttggaa     240
gacctgttaa tgggcacact aggaattgtg tgccccatct gttctcagaa acca           294

<210> SEQ ID NO 4
<211> LENGTH: 98
<212> TYPE: PRT
<213> ORGANISM: Human papillomavirus type 16

<400> SEQUENCE: 4

Met His Gly Asp Thr Pro Thr Leu His Glu Tyr Met Leu Asp Leu Gln
1               5                   10                  15

Pro Glu Thr Thr Gly Leu Tyr Gly Tyr Gly Gln Leu Ser Asp Ser Ser

```
              20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                85                  90                  95

Lys Pro

<210> SEQ ID NO 5
<211> LENGTH: 23
<212> TYPE: PRT
<213> ORGANISM: respiratory syncytial virus

<400> SEQUENCE: 5

Asn Lys Leu Ser Glu Tyr Asn Val Phe His Asn Lys Thr Phe Glu Leu
 1               5                  10                  15

Pro Arg Ala Arg Val Asn Thr
            20

<210> SEQ ID NO 6
<211> LENGTH: 386
<212> TYPE: PRT
<213> ORGANISM: Artificial Sequence
<220> FEATURE:
<223> OTHER INFORMATION: PspA-SH fusion protein

<400> SEQUENCE: 6

Glu Glu Ser Pro Val Ala Ser Gln Ser Lys Ala Glu Lys Asp Tyr Asp
 1               5                  10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
 50                  55                  60

Glu Glu Met Asp Lys Ala Val Ala Ala Val Gln Gln Ala Tyr Leu Ala
 65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Asp Tyr Ala Lys Glu Gly Phe
        195                 200                 205
```

-continued

```
Arg Ala Pro Leu Gln Ser Lys Leu Asp Ala Lys Ala Lys Leu Ser
            210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285

Pro Glu Lys Pro Ala Pro Ala Pro Glu Thr Pro Ala Pro Glu Gly Gly
290                 295                 300

Gly Gly Ser Asn Lys Leu Ser Glu Tyr Asn Val Phe His Asn Lys Thr
305                 310                 315                 320

Phe Glu Leu Pro Arg Ala Arg Val Asn Thr Gly Gly Gly Ser Asn
                325                 330                 335

Lys Leu Ser Glu Tyr Asn Val Phe His Asn Lys Thr Phe Glu Leu Pro
            340                 345                 350

Arg Ala Arg Val Asn Thr Gly Gly Gly Gly Ser Asn Lys Leu Ser Glu
        355                 360                 365

Tyr Asn Val Phe His Asn Lys Thr Phe Glu Leu Pro Arg Ala Arg Val
370                 375                 380

Asn Thr
385
```

```
<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Gly Gly Gly Gly Ser
1               5
```

```
<210> SEQ ID NO 8
<211> LENGTH: 274
<212> TYPE: PRT
<213> ORGANISM: Artificial Sequence
<220> FEATURE:
<223> OTHER INFORMATION: ESAT&-Rv2660-Rv0288 fusion

<400> SEQUENCE: 8

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala Gly
                85                  90                  95

Pro Gly Pro Gly Ile Ala Gly Val Asp Gln Ala Leu Ala Ala Thr Gly
            100                 105                 110
```

```
Gln Ala Ser Gln Arg Ala Ala Gly Ala Ser Gly Gly Val Thr Val Gly
            115                 120                 125

Val Gly Val Gly Thr Glu Gln Arg Asn Leu Ser Val Val Ala Pro Ser
            130                 135                 140

Gln Phe Thr Phe Ser Ser Arg Ser Pro Asp Phe Val Asp Glu Thr Ala
145                 150                 155                 160

Gly Gln Ser Trp Cys Ala Ile Leu Gly Leu Asn Gln Phe His Gly Pro
                165                 170                 175

Gly Pro Gly Ser Gln Ile Met Tyr Asn Tyr Pro Ala Met Leu Gly His
            180                 185                 190

Ala Gly Asp Met Ala Gly Tyr Ala Gly Thr Leu Gln Ser Leu Gly Ala
            195                 200                 205

Glu Ile Ala Val Glu Gln Ala Ala Leu Gln Ser Ala Trp Gln Gly Asp
            210                 215                 220

Thr Gly Ile Thr Tyr Gln Ala Trp Gln Ala Gln Trp Asn Gln Ala Met
225                 230                 235                 240

Glu Asp Leu Val Arg Ala Tyr His Ala Met Ser Ser Thr His Glu Ala
                245                 250                 255

Asn Thr Met Ala Met Met Ala Arg Asp Thr Ala Glu Ala Ala Lys Trp
            260                 265                 270

Gly Gly

<210> SEQ ID NO 9
<211> LENGTH: 822
<212> TYPE: DNA
<213> ORGANISM: Artificial Sequence
<220> FEATURE:
<223> OTHER INFORMATION: Syntetic nucleotide

<400> SEQUENCE: 9
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt cgcaggacc aggtcctgga      300 atagcgggcg tcgaccaggc gcttgcagca acaggccagg ctagccagcg ggcggcaggc     360
gcatctggtg gggtcaccgt cggtgtcggc gtgggcacgg aacagaggaa cctttcggtg     420
gttgcaccga gtcagttcac atttagttca cgcagcccag attttgtgga tgaaaccgca     480
ggtcaatcgt ggtgcgcgat actgggattg aaccagtttc acggaccagg tcctggatcg     540
caaatcatgt acaactaccc cgcgatgttg ggtcacgccg gggatatggc cggatatgcc     600
ggcacgctgc agagcttggg tgccgagatc gccgtggagc aggccgcgtt gcagagtgcg     660
tggcagggcg ataccgggat cacgtatcag gcgtggcagg cacagtggaa ccaggccatg     720
gaagatttgg tgcgggccta tcatgcgatg tccagcaccc atgaagccaa caccatggcg     780
atgatggccc gcgacacggc cgaagccgcc aaatggggcg gc                        822
```